United States Patent [19]

Howe

[11] 4,210,762
[45] Jul. 1, 1980

[54] 2[5-(3-TRIFLUOROMETHYLPHENYL)-1,3,4-OXADIAZOL-2-YL] BENZOATES

[75] Inventor: Robert K. Howe, Bridgeton, Mo.

[73] Assignee: Monsanto Company, St. Louis, Mo.

[21] Appl. No.: 934,440

[22] Filed: Aug. 17, 1978

[51] Int. Cl.$^2$ .................... C07D 271/10; A01N 9/22
[52] U.S. Cl. ........................ 548/145; 71/92; 548/235; 548/262
[58] Field of Search ................... 260/307 G

[56] References Cited
U.S. PATENT DOCUMENTS

| | | |
|---|---|---|
| 3,192,103 | 6/1965 | Sousa et al. ............... 71/76 |
| 3,211,742 | 10/1965 | Lenaers ..................... 260/307 |
| 3,772,284 | 11/1973 | Singh et al. ................ 260/239 A |
| 3,822,138 | 5/1975 | Brouwer et al. ............ 260/307 G |
| 3,947,263 | 3/1976 | Brouwer et al. ............ 260/307 G |
| 3,987,179 | 10/1976 | Nadelson ................... 260/307 H X |
| 4,016,170 | 4/1977 | Nadelson ................... 260/307 H |
| 4,032,644 | 6/1977 | Nadelson ................... 260/307 H |
| 4,035,175 | 7/1977 | Brouwer et al. ............ 71/76 |
| 4,055,409 | 10/1977 | Johnson et al. ............ 71/76 |
| 4,135,910 | 1/1979 | Howe ........................ 260/307 G X |

FOREIGN PATENT DOCUMENTS 1494877 12/1977 United Kingdom ............... 260/307 G

OTHER PUBLICATIONS

Beyer et al., "Plant Physiol.", (1976), vol. 57, pp. 839–841.
Geissler et al., "Pestic. Sci.", vol. 6, (1975), pp. 441–450.

Primary Examiner—Anton H. Sutto
Attorney, Agent, or Firm—Patricia A. Coburn; Donald W. Peterson

[57] ABSTRACT

The invention relates to compounds of the formula

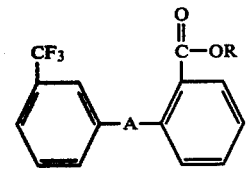

wherein R is H, lower alkyl or agriculturally acceptable cations; and wherein A is a 1,3,4-oxadiazol, 1,3-oxazole and 1,3,4-triazole which are useful as plant growth regulators.

4 Claims, No Drawings

2[5-(3-TRIFLUOROMETHYLPHENYL)-1,3,4-OXADIAZOL-2-YL] BENZOATES

BACKGROUND OF THE INVENTION

It is known in the art that certain diphenylheterocyclic compounds possess plant growth regulant activity. Belgian Pat. No. 837,454, July 9, 1976, discloses that certain isoxazol-3,5-yl, thiazol-2,4-yl, 1,2,4-triazol-3,5-yl, 1,3,4-thiadiazol or 1,2,4- or 1,3,4-oxadiazolyl compounds are useful in regulating the growth of plants. U.S. Pat. No. 3,471,509 teaches that certain oxadiazole, oxazole and thiadiazol benzoic acids or benzoates are plant growth regulants. These patents do not however teach the substitution of the phenyl radical attached to the parent heterocyclic nucleus with a trifluoromethyl moiety. Further, there seems to be no recognition in the art that substitution of a trifluoromethyl moiety at the meta position of the phenyl ring unexpectedly enhances the biological activity of the parent heteroaryl benzoate nucleus.

DESCRIPTION OF THE INVENTION

It has been discovered that the plant growth regulant effect of certain heteroarylbenzoates is unexpectedly enhanced by the substitution of a trifluoromethyl radical at the meta position of the phenyl group attached to the heterocyclic nucleus of compounds corresponding to the following formula

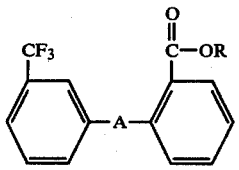

wherein R is H, lower alkyl, or agriculturally acceptable cations; A is

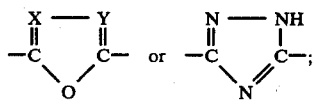

X and Y independently equal N or CH but cannot both equal CH simultaneously.

When used herein, the term "lower alkyl" includes those members including straight and branched chain, having from 1 to 5 carbon atoms inclusive, for example, methyl, ethyl, n-propyl, isopropyl, n-butyl, sec-butyl, tert-butyl, n-pentyl, isopentyl, and the like.

When A represents

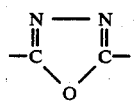

the compounds formed thereby are 1,3,4-oxadiazol-2-yl benzoates; when A is

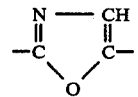

the compounds formed thereby are 5-yl and 2-yl 1,3-oxazole benzoates; 1,2,4-triazol-3,5-yls are formed when A is

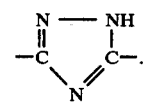

The term "agriculturally acceptable cations" is understood to mean those cations which are commonly used in plant growth regulant compositions to form the salt of the free acid, including but not limited to the alkali metal, substituted amine and ammonium cations.

The following may be mentioned as examples of the active oxadiazoles, oxazoles and triazoles useful in regulating the growth of leguminous plants in accordance with the present invention: 2-[5-(3-trifluoromethylphenyl)-1,3,4-oxadiazol-2-yl]benzoic acid, methyl 2-[5-(3-trifluoromethylphenyl)-1,3,4-oxadiazol-2-yl]benzoate, ethyl 2-[5-(3-trifluoromethylphenyl)-1,3,4-oxadiazol-2-yl]benzoate, 2-[5-(3-trifluoromethylphenyl)-1,2,4-triazol-3-yl]benzoic acid, methyl 2-[5-(3-trifluoromethylphenyl)-1,2,4-triazol-3-yl]benzoate, 2-[5-(3-trifluoromethylphenyl)-1,3-oxazol-2-yl]benzoic acid, methyl 2-[5-(3-trifluoromethylphenyl)-1,3-oxazol-5-yl]benzoate.

The term "active ingredient" is used herein to describe the m-trifluoromethyl substituted heteroaryl benzoates of the formula previously described. Various methods can be used to prepare the heteroaryl benzoates of the present invention, which are useful in regulating the growth of leguminous plants. The following methods and examples describe the preparation of these compounds in greater detail.

The 1,3,4-oxadiazol-3-yl compounds can be pepared according to the following general reaction:

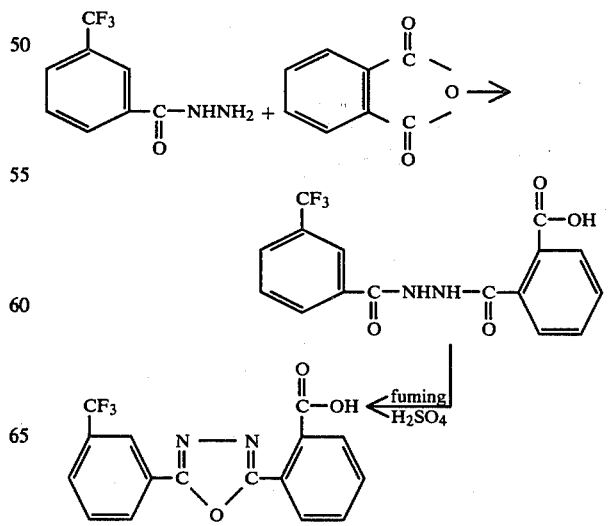

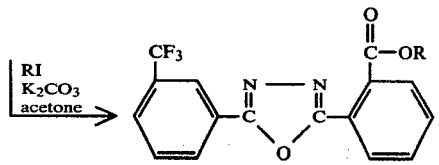

Examples 1, 2 and 3 describe in detail the preparation of several specific 1,3,4-oxadiazoles.

EXAMPLE 1

2-[5-(3-Trifluoromethylphenyl)-1,3,4-Oxadiazol-2-yl]Benzoic Acid.

Powdered 1-(2-carboxybenzoyl)-2-(3-trifluoromethylbenzoyl) hydrazine (50 g, 0.142 mol) was added in portions, over a 40 minute period, to 100 ml of vigorously stirred, pre-cooled, fuming sulfuric acid (20%) at $-5°$ C. to $-1°$ C. under nitrogen. The reaction mixture was stirred at $0°-5°$ C. for 2 hours, then poured into 1.2 liters of ice-water. The solid collected was washed with water, heated in saturated $NaHCO_3$ solution (2 liters) at 50° C. and filtered. The filtrate was acidified with concentrated HCl to give 2.75 g of solid; mp 141°–159° C. The solid which was filtered off from the original $NaHCO_3$ solution, was heated once again in saturated $NaHCO_3$ at 60° C. and the solution filtered. Upon acidification of the filtrate with concentrated HCl, 9.3 g of solid was collected, mp 159°–161.5° C. Crystallization of 3.5 g of this material from acetonitrile gave 1.6 g of white solid, mp 165°–168° C.

Anal. Calc'd for $C_{16}H_9F_3N_2O_3$: C, 57.49; H, 2.71; Found: C, 57.38, H, 2.75.

EXAMPLE 2

Methyl 2-[5-(3-Trifluoromethylphenyl)-1,3,4-Oxadiazol-2-yl]Benzoate.

A mixture of 2-[5-(3-trifluoromethylphenyl)-1,3,4-oxadiazol-2-yl]benzoic acid (8 g, 0.024 mol), methyl iodide (7.1 g, 0.05 mol), potassium carbonate (12 g) and acetone (100 ml) was held at reflux for 30 hours, cooled and filtered. The filtrate was concentrated to an oil. The oil was dissolved in 300 ml of ether and the ethereal solution was washed three times with water, dried over $CaSO_4$ and concentrated to give 7.45 g (89.3%) of crude solid as a yellow oil. The yellow oil was crystallized from a toluene-heptane solution to afford 6.5 g of white crystals; mp 83°–84° C.; NMR ($CDCl_3$) & 3.83 (s,3H), 7.28–8.32 (m,8H); ir ($CHCl_3$) 1725 $cm^{-1}$.

Anal. Calc'd for $C_{17}H_{11}F_3N_2O_3$: C, 58.63; H, 3.18; Found: C, 58.65; H, 3.18.

EXAMPLE 3

Ethyl 2-[5-(3-Trifluoromethylphenyl)-1,3,4-Oxadiazol-2-yl]Benzoate.

This compound was prepared as described in Example 2, except that ethyl iodide was used.

The 1,3-oxazoles were prepared using the general procedure described in U.S. Pat. No. 3,882,138, herein incorporated by reference, except that α-bromo-3-trifluoromethylacetophenone was used in place of α-bromoacetophenone. The α-bromo-3-trifluoromethylacetophenone starting material was prepared as described in Example 4.

EXAMPLE 4

α-Bromo-3-Trifluoromethylacetophenone.

A mixture of ethyl acetate (417 ml), chloroform (417 ml) and cupric bromide (186.1 g, 0.833 mol) was heated to reflux and vigorously stirred in a 4-necked flask fitted with a bubbler. 3-Trifluoromethylacetophenone (94.1 g, 0.5 mol) was poured into the mixture. Aliquots were withdrawn from time to time for NMR analysis. After a total of 5.5 hours at reflux and 38 hours at room temperature about 71% of the monobromoacetophenone was formed. Another 26.8 g (0.12 mol) of cupric bromide was added. The mixture was held at reflux for an additional 4 hours and at room temperature for 18 hours and filtered. The filtrate was concentrated under vacuum to a mixture of an oil and solid. 300 ml of chloroform was added to the mixture and the solid was filtered off. The chloroform solution was concentrated to give 111.7 g of brown oil. The oil contained 87% of the final product and 13% starting material according to NMR analysis.

EXAMPLE 5

2-[5-(3-Trifluoromethylphenyl)-1,3-Oxazol-2-yl]Benzoic Acid.

N-(3-trifluoromethylphenacyl) phthalamic acid (9.4 g, 0.027 mol) was added portionwise to conc. sulfuric acid (30 ml) at <10° C. The resultant solution was stirred for 20 hours at room temperature and poured into 600 ml of ice-water to yield 8.2 g of crude 2-[5-(3-trifluoromethylphenyl)-1,3-oxazol-2-yl]benzoic acid as a brown solid; ir ($CHCl_3$) 1720 $cm^{-1}$. The crude acid was used for subsequent synthesis is obtained.

EXAMPLE 6

Methyl 2-[5-(3-Trifluoromethylphenyl)-1,3Oxazol-2-yl]Benzoate.

A mixture of 2-[5-(3-trifluoromethylphenyl)-1,3-oxazol-2-yl]benzoic acid (8 g, 0.024 mol), methyl iodide (7.1 g, 0.05 mol), potassium carbonate (12 g) and acetone (100 ml) was held at reflux for 30 hours, cooled and filtered. The filtrate was concentrated to an oil. The oil was dissolved in 300 ml of ether and the ethereal solution was washed three times with water, dried over $CaSO_4$ and concentrated to give 7.8 g (9.2% yield) of an oil. The crude product obtained was chromatographed on silica gel with ethyl acetate as the eluent, and then recrystallized from a toluene-heptane solution to give methyl 2-[5-(3-trifluoromethylphenyl)-1,3-oxazol-2-yl]benzoate as a white solid; mp 92.5°–94° C.; NMR ($CDCl_3$) & 3.90 (s, 3H), 7.12–8.62 (m,9H); ir ($CHCl_3$) 1725 $cm^{-1}$.

Anal. Calc'd for $C_{18}H_{12}F_3NO_3$: C, 62.25; H, 3.48; Found: C, 62.37; H, 3.54;

The 1,3-oxazol-5-yl compounds were prepared by a photochemical rearrangement process from the corresponding 1,2-isoxazol-5-yl isomers. Example 7 describes the preparation of methyl 2-[3-(3-trifluoromethylphenyl)-1,2-isoxazol-5-yl]benzoate in detail. This same method can be used to prepare other lower alkyl 2-[3-(3-trifluoromethylphenyl)-1,2-isoxazol-5-yl]benzoates using the appropriate lower alkyl o-vinyl benzoate.

EXAMPLE 7

Preparation of Methyl 2-[3-(3-(TrifluoromethylPhenyl)-1,2-Isoxazol-5-yl]Benzoate.

A solution of 8.67 g (0.0858 mol) of triethylamine in 25 ml of ether was added dropwise with stirring to a solution of 19.19 g (0.0858 mol) of m-trifluoromethylbenzohydroxamoyl chloride and 13.9 g (0.0858 mol) of methyl o-vinylbenzoate in 200 ml of ether at 0°–5° C. over a 45 minute period. The mixture was stirred in an ice bath for 2 hours and then at 20° C. for 21 hours, and then was washed three times with water. The ether layer was filtered to remove a little gelatinous solid, and the filtrate was dried ($CaSO_4$) and concentrated under vacuum to 10 torr at 60° C. to give 29.5 g (98%) of oil, methyl 2-[3-(3-trifluoromethylphenyl)-2-isoxazolin-5yl]benzoate.

A solution of 26.74 g (0.0766 mol) of the isoxazolin from above and 13.6 g (0.0766 mol) of N-bromosuccinimide in 250 ml of $CCl_4$ was heated with stirring at reflux. A 0.5 g sample of benzoyl peroxide was added; after 10–15 minutes the red color of $Br_2$ was evident. After the reaction mixture was held at reflux for 1 hour, another 0.1 g of benzoyl peroxide was added, and heating was continued for another hour. The reaction mixture was allowed to cool and was filtered free of succinimide. The filtrate was concentrated under vacuum, and the residual oil was subjected to Kugelrohr distillation at 140°–170° C. (0.2 torr); a temporary loss of vacuum to 1–2 mm occurred when the pot temperature reached 140° C., and a sour smell emitted from the oil pump, indicative of HBr evolution. The distillate was subjected to another Kugelrohr distillation to give 20.01 g of 98% pure product as a viscous oil. Crystallization of the oil from ether-hexane at 0° C. gave 13.86 g of solid, mp 46.5°–48.5° C.

Anal. Calc'd for $C_{18}H_{12}F_3NO_3$: C, 62.25; H, 3.48; N, 4.03; Found: C, 62.33; H, 3,49; N, 4.09.

EXAMPLE 8

Methyl 2-[2-(3-Trifluoromethylphenyl)-1,3-Oxazol-5-yl]Benzoate.

Methyl 2-[3-(3-trifluoromethylphenyl)-5-isoxazolyl]-benzoate (4.12 g, 0.012 mol) in acetonitrile (380 ml) was irradiated with low pressure mercury lamps in a Rayonet photochemical reactor at room temperature for 10 hours. NMR spectrum of an aliquot indicated that the reaction was complete. The photolysate was concentrated under vacuum to give 3.98 g of a yellow solid material which contained at least 85% of the desired product according to a VPC analysis. The solid material was passed through a silica gel column (50% ethyl acetate-50% cyclohexane) to give 3.48 g of pale yellow crystals; mp 63°–72° C. Recrystallization of the crystals once from toluene-hexane and once from hexane yielded 2.22 g of pure methyl 2-[2-(3-trifluoromethylphenyl)-1,3-oxazol-5-yl]benzoate as white crystals; mp 84.5°–86° C.; NMR ($CDCl_3$) & 3.80 (s,3H), 7.38 (s,1H), 7.38–8.25 (m,8H); ir ($CHCl_3$) 1724 cm$^{-1}$.

Anal. Calc'd for $C_{18}H_{12}F_3NO_3$: C, 62.25; H, 3.48; Found: C, 62.11; H, 3.49.

2-[5-(3-trifluoromethylphenyl)-1,2,4-triazol-3-yl]benzoates can be prepared according to the procedure described in Belgian Pat. No. 837,454 (issued July 9, 1976), herein incorporated by reference, by using 3-trifluoromethylbenzonitrile as the starting benzonitrile.

EXAMPLE 9

2-[5-(3-Trifluoromethylphenyl)-1,2,4-Triazol-3-yl]Benzoic Acid.

A solution of 3-(3-trifluoromethylphenyl)-5-(2-methylphenyl)-1,2,4-triazol (6.3 g, 0.021 mol), potassium permanganate (15 g, 0.095 mol) and 10% sodium hydroxide solution (100 ml) was held at reflux for one hour, cooled and filtered through celite. The filtrate was acidified with concentrated HCl and the solid precipitate was collected. The solid was washed with ether to give 2.2 g of 2-[5-(3-trifluoromethylphenyl)-1,2,4-triazol-3-yl]benzoic acid in 32% yield, mp ~200°.

EXAMPLE 10

Methyl 2-[5-(3-trifluoromethylphenyl)-1,2,4-Triazol-3-yl]Benzoate.

2.2 gm of 2-[5-(3-trifluoromethylphenyl)-1,2,4-triazol-3-yl]benzoic acid was heated with 0.5 ml of concentrated $H_2SO_4$ and 50 ml of methanol and held at reflux for 28 hours. The solution was then cooled and poured into 500 ml of ice-water. The mixture was extracted twice with ether (total volume 800 ml), dried over $CaSO_4$, and concentrated under vacuum to afford an oil. The oil was chromatographed on a silica gel column using ethyl acetate as eluent. The oil was collected from the column and crystallized from toluene/heptane to give 1.92 gm of white crystals; m.p. 110.5°–112° C.; NMR ($CDCl_3$) & 3.91 (s,3H), 7.14–8.46 (m,8H); ir ($CHCl_3$) 3440, 3320, 1710 cm$^{-1}$.

Anal. Calc'd for $C_{17}H_{12}F_3N_3O_2$: C, 58.79; H, 3.48; Found: C, 58.79; H, 3.50.

As noted above, the compounds of the present invention have been found to be effective in the regulation of plant growth, especially legumes. The preferred legume to be regulated is soybean (Glycine max).

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. The above changes may be characterized as an acceleration or retardation of plant growth, stature reduction, leaf or canopy alteration, axillary bud growth or inhibition, darker foliar color, and the like. Many of these modifications are desirable in and of themselves, for example, dark foliar color, grossly observable as darker green leaves, may be indicative of higher chlorophyll activity and thus an improved or enhanced rate of photosynthesis. Altered canopy and leaf alteration are responses directed toward altering a plant's leaf display thereby allowing the plant to better utilize light, which allows for enhanced photosynthesis. Enhancement of photosynthesis at the appropriate stage of the plant's growth and development may enable the plant to fix more carbon dioxide resulting in the production of increased amounts of carbohydrates, amino acids, etc., which could be available for utilization in the plant's reproductive activities, leading to increased plant crop yields.

Other of the plant growth regulant responses may be more valuable for their economic effects. For example, a reduction in stature of the plant permits the growing of more plants per unit area.

It is to be understood that the regulation of desirable leguminous crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species or variety of plant and its stage of development, the plant growth medium and whether a permanent or transitory effect is sought.

In accordance with this invention, it has been found that desirable modification of leguminous crop plants is achieved by applying the above-described plant regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In accordance with the practice of the invention, several plant growth regulating compositions were formulated by mixing various m-trifluoromethyl heteroaryl benzoate compounds as the active ingredient, with water, acetone and surfactant. The compositions thus formulated exhibited plant regulatory properties as illustrated by the test set forth in Example 11.

EXAMPLE 11

Soybean plants, variety Clark 63, were grown in a growth chamber at 27° C. When the plants reached the ½ expanded unifoliate leaf stage (approximately 8 days) they were dip-treated into an aqueous solution of active ingredient, acetone, cyclohexanone and Emulsifier L. The treated plants were allowed to grow in a growth chamber and greenhouse at temperatures of 14° to 24° C. for an additional 4 weeks. Effects on growth were observed and recorded during the period 4 weeks after treatment. Plants treated with water containing acetone, cyclohexanone and Emulsifier L were grown in the manner described and served as the control. The observations made and recorded in accordance with Example 11 are shown in Table I.

Table I

| Compound of Ex. No. | Rate ppm | Observations |
|---|---|---|
| 2 | 266 | Stature reduction, inhibition of apical development, axillary bud growth, leaf epinasty, reduced leaf size, dark foliar color, leaf curl. |
| 6 | 266 | Stature reduction, axillary bud growth, reduced leaf size, apical leaf enhancement, darker green leaves, leaf curl. |
| 8 | 266 | Stature reduction, leaf epinasty, reduced leaf size, leaf curl. |
| 10 | 266 | Stature reduction, axillary bud growth, leaf epinasty, reduced leaf size, dark foliar color, leaf curl. |

EXAMPLE 12

A number of soybean plants, variety Williams, were grown from seeds in plastic pots in the greenhouse for a period of one week at which time the plants were thinned to one plant per pot. When the second trifoliate leaf (three weeks) was fully expanded, the plants were treated with a solution of the active ingredient in acetone and water. Aqueous Tween 20 was used as a surfactant.

When the fifth trifoliate leaf (four to five weeks) was fully expanded, the treated plants were compared with the non-treated control plants and the observations recorded.

Table II below summarizes the results and observations made in accordance with the above procedure.

Table II

| Compound of Ex. No. | RATE Lbs Acre | RATE Kilos Hectare | Response |
|---|---|---|---|
| 1 | 0.1 | 0.112 | Stature reduction, leaf alteration, leaf alteration new growth, leaf inhibition, axillary bud inhibition, inhibited dry wt. |
|  | 0.5 | 0.56 | Stature reduction, leaf alteration, leaf alteration new growth, leaf inhibition, axillary bud inhibition, inhibited dry wt. |
|  | 2.5 | 2.80 | Stature reduction, leaf alteration, leaf alteration new growth, leaf inhibition, axillary bud inhibition, inhibited dry wt., slight leaf burn. |
| 2 | 0.1 | 0.112 | Stature reduction, leaf distortion, leaf inhibition, inhibited dry wt., leaf distortion new growth, slight leaf burn. |
|  | 0.5 | 0.56 | Stature reduction, leaf distortion, leaf inhibition, inhibited dry wt., leaf distortion new growth, slight leaf burn. |
|  | 2.5 | 2.80 | Stature reduction, leaf distortion, leaf inhibition, inhibited dry wt., leaf distortion new growth, slight leaf burn. |

In selecting the appropriate time and rate of application of the active ingredient, it will be recognized that precise rates will also be dependent upon the desired response, mode of application, plant variety, soil conditions and various other factors known to those skilled in the art. While a rate of up to 11.2 kilos per hectare may be used, rates from about 0.056 to about 6.72 kilos per hectare are preferred. In addition, it will be recognized that single or multiple applications may be used to exert the desired response.

In the practice of the invention, the active ingredient can be used alone or in combination with materials referred to in the art as adjuvants, in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 5 to 95 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

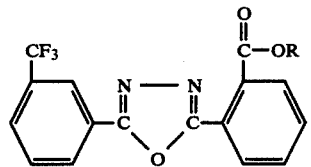

wherein R is H, lower alkyl or agriculturally acceptable cations

2. A compound according to claim 1 wherein R is lower alkyl.

3. A compound according to Claim 1 which is methyl 2-[5-(3-trifluoromethylphenyl)-1,3,4-oxadiazol-2-yl] benzoate.

4. A compount according to claim 1 which is 2-[5-3-trifluoromethylphenyl)-1,3,4-oxadiazol-2-yl] benzoic acid

* * * * *